United States Patent [19]

Kondo et al.

[11] 4,229,593
[45] Oct. 21, 1980

[54] METHOD TO PREPARE (+)-CIS-3-(2,2-DICHLOROETHENYL)-2,2-DIMETHYLCYCLOPROPANECARBOXYLIC ACID

[75] Inventors: Kiyoshi Kondo, Kanagawa; Minoru Suda, Sagami Hara, both of Japan

[73] Assignee: FMC Corporation, Philadelphia, Pa.

[21] Appl. No.: 43,599

[22] Filed: May 29, 1979

[51] Int. Cl.³ .............................................. C07C 61/40
[52] U.S. Cl. ............................. 562/401; 260/501.16; 546/134; 562/506
[58] Field of Search ................ 562/401, 506; 546/134; 260/570.6, 501.16

[56] References Cited

U.S. PATENT DOCUMENTS

| | | | |
|---|---|---|---|
| 3,282,985 | 11/1966 | Matsui et al. | 546/134 X |
| 3,646,118 | 2/1972 | Goffinet et al. | 562/401 |
| 3,666,798 | 5/1972 | Matsui et al. | 562/401 |
| 3,739,019 | 6/1973 | Veda et al. | 562/401 |
| 3,786,070 | 1/1974 | Martel et al. | 562/401 X |
| 3,842,125 | 10/1974 | Horiuchi et al. | 562/401 |
| 3,879,451 | 4/1975 | Yoshioka et al. | 562/401 |
| 4,014,918 | 3/1977 | Martel | 562/401 X |
| 4,024,163 | 5/1977 | Elliott et al. | 260/347.4 |

FOREIGN PATENT DOCUMENTS

| | | | |
|---|---|---|---|
| 51-36441 | 3/1976 | Japan . | |
| 51-143647 | 5/1976 | Japan . | |
| 1178423 | 1/1979 | United Kingdom | 562/506 |
| 2008589 | 6/1979 | United Kingdom | 562/506 |

OTHER PUBLICATIONS

Campbell, I., et al., *J. Chem. Soc.*, 283 (1945).
*Chemical Abstracts*, 52:13650e (1958) [Farkas, J., et al., *Chem. Listy* 52, 688-694 (1958)].
March, J., *Advanced Organic Chemistry*, 2nd Edition, McGraw-Hill, New York, 1977, pp. 108-109.
Campbell, I., et al., *J. Sci. Food Agric.*, 3, 189 (1952).

*Primary Examiner*—Henry R. Jiles
*Assistant Examiner*—Richard A. Schwartz
*Attorney, Agent, or Firm*—Richard L. Hansen; Henry R. Ertelt

[57] ABSTRACT

Process to prepare 3-(2,2-dichloroethenyl)-2,2-dimethylcyclopropanecarboxylic acid enriched with the (+)-cis isomer.

4 Claims, No Drawings

METHOD TO PREPARE (+)-CIS-3-(2,2-DICHLOROETHENYL)-2,2-DIMETHYLCYCLOPROPANECARBOXYLIC ACID

This invention relates to a process to prepare (+)-cis-3-(2,2-dichloroethenyl)-2,2-dimethylcyclopropanecarboxylic acid, from which pyrethroid insecticides are made, and to intermediates useful in the process.

U.S. Pat. No. 4,024,163, which is incorporated herein by reference, discloses novel insecticidal esters prepared from 3-(2,2-dichloroethenyl)-2,2-dimethylcyclopropanecarboxylic acid. This acid exhibits both geometrical and optical isomerism, the four isomers being designated (+)-cis, (−)-cis, (+)-trans, and (−)-trans. Among these various isomers, the (+)-cis isomer yields the most efficacious esters. Therefore, processes capable of economically producing the (+)-cis isomer are being sought. The commercial processes for making the acid generate racemic mixtures of the cis and trans isomers, and an economical process for separating from such mixtures acid enriched in the desired (+)-cis isomer is needed.

This separation generally has been effected in two stages; for example, the cis and trans isomers, with different physical properties, are separated by fractional crystallization; then the cis or trans racemic mixtures are resolved separately by salt formation with an optically active amine, separation of the two salt diasteriomers, and hydrolysis to regenerate the optically active acids [See U.S. Pat. No. 4,024,163 and Japan. Kokai 51 036,441]. Obviously, it would be more economical to separate the desired (+)-cis isomer directly in one step from the racemic cis,trans mixture.

However, the prior art suggests that this is not possible. According to Japan. Kokai 51 143,647, treatment of a racemic cis,trans mixture (cis/trans=45/55) of the acid with optically active β-dimethylamino-α,α-dimethyl-β-phenethyl alcohol leads to a separated amine salt which is 89.6% (+)-trans acid and only 8% (+)-cis acid, upon hydrolysis.

It has now been found, quite unexpectedly, that when the racemic cis,trans acid is treated with certain optically active amines, one of which is an isomer of the β-dimethylamino-α,α-dimethyl-β-phenethyl alcohol disclosed in the prior art, a salt is obtained which hydrolyses to an acid containing predominately the desirable (+)-cis isomer. That is, the process of this invention is a method to prepare 3-(2,2-dichloroethenyl)-2,2-dimethylcyclopropanecarboxylic acid containing at least 50% (+)-cis isomer which comprises neutralizing racemic cis,trans-3-(2,2-dichloroethenyl)-2,2-dimethylcyclopropanecarboxylic acid containing at least 40 percent cis isomers with an alkaloid base selected from l-ephedrine or quinine in a solvent selected from ethyl acetate or acetonitrile, cooling the resulting solution, isolating the precipitated salt, and hydrolyzing the salt to produce the enriched acid.

The intermediate compounds of this invention constitute the novel l-ephedrine and quinine salts of (2,2-dichloroethenyl)-2,2-dimethylcyclopropanecarboxylic acid.

In carrying out the process of this invention it is preferred to employ approximately equimolar amounts of the acid and alkaloid base, but less than an equimolar amount of alkaloid base, to about one half molar equivalent, also gives satisfactory results. Although either solvent may be employed with both l-ephedrine and quinine, it is preferred to use ethyl acetate with quinine and acetonitrile with l-ephedrine. The invention will be understood more completely by reference to the following Examples.

EXAMPLE 1

Preparation of (+)-cis-3-(2,2-dichloroethenyl)-2,2-dimethylcyclopropanecarboxylic acid via the quinine salt Quinine.$3H_2O$ (1.52 g, 4.0 mmol) and a 1:1 cis:trans mixture of racemic cis,trans-3-(2,2-dichloroethenyl)-2,2-dimethylcyclopropanecarboxylic acid (840 mg, 4.0 mmol) were dissolved in hot ethyl acetate (60 ml). After cooling to and standing at room temperature for one day, a precipitate was collected by filtration and recrystallized from ethyl acetate (14 ml). The recrystallized salt was washed three times with 1 N aqueous hydrochloric acid, hydrolyzing the salt, and the product was dissolved in diethyl ether (30 ml). The ethereal solution was washed successively with 1 N aqueous hydrochloric acid solution and saturated aqueous sodium chloride, then dried over magnesium sulfate. The ether was distilled under vacuum to afford the free acid. The 3-(2,2-dichloroethenyl)-2,2-dimethylcyclopropanecarboxylic acid was treated with thionyl chloride (500 mg, 4.2 mmol). The excess thionyl chloride was distilled under vacuum, and the residue was dissolved in toluene (1 ml). The resultant solution was added to a solution of 1-2-octanol (135 mg, 1 mmol) and pyridine (80 mg, 1 mmol) in toluene (1 ml), and the mixture was heated at 40° C. for 1 hr. Analysis of the reaction mixture after an hour by vapor phase chromatography against authentic samples indicated that the molar ratio of isomers (+)-cis: (−)-cis: (+)-trans: (−)-trans was 93.6:1.3:4.9:0.3.

EXAMPLE 2

Preparation of (+)-cis-3-(2,2-dichloroethenyl)-2,2-dimethylcyclopropanecarboxylic acid via the l-ephedrine salt l-Ephedrine (340 mg, 2 mmol) and a 1:1 cis:trans mixture of racemic cis,trans 3-(2,2-dichloroethenyl)-2,2-dimethylcyclopropanecarboxylic acid (420 mg, 2 mmol) were dissolved in hot acetonitrile (15 ml). An additional 114 mg of l-ephedrine (0.67 mmol) was added. After cooling, the resulting precipitate was added to 1 N aqueous hydrochloric acid (6 ml), hydrolyzing the salt, and the mixture was extracted with diethyl ether. The organic layer was washed with 1 N hydrochloric acid, then with saturated aqueous sodium chloride and dried over magnesium sulfate. The solvent was distilled under vacuum. Thionyl chloride (400 mg, 3.4 mmol) was added to the residue, and the reaction mixture was heated to 40° C. and stirred for 30 minutes. The excess thionyl chloride was distilled under vacuum, and the residue, containing the acid chloride, was dissolved in toluene (1 ml). The toluene solution was added to a solution of 1-2-octyl alcohol (100 mg, 0.77 mmol) and pyridine (100 mg). Analysis of the reaction mixture after one hour as in Example 1 indicated the isomer ratio (+)-cis: (−)-cis: (+)-trans: (−)-trans was 77.8:1.1:18.1:3.0.

We claim:

1. A method to prepare 3-(2,2-dichloroethenyl)-2,2-dimethylcyclopropanecarboxylic acid containing at least 50% (+)-cis isomer which comprises neutralizing racemic cis, trans-3-(2,2-dichloroethenyl)-2,2-dimethylcyclopropanecarboxylic acid containing at least 40 percent cis isomers with an alkaloid base selected from l-ephedrin or quinine in a solvent selected from ethyl acetate or acetonitrile, cooling the resulting solution, isolating the precipitated salt, and hydrolyzing the salt to produce the enriched acid.

2. The method of claim 1 wherein the acid and alkaloid base are employed in approximately equimolar amounts.

3. The method of claim 1 wherein the alkaloid base is quinine and the solvent is ethyl acetate.

4. The method of claim 1 wherein the alkaloid base is l-ephedrine and the solvent is acetonitrile.

* * * * *